United States Patent [19]

Robins et al.

[11] Patent Number: 5,599,847

[45] Date of Patent: Feb. 4, 1997

[54] ANTIFUNGAL COMPOUNDS

[75] Inventors: David J. Robins, Glasgow; Dale R. Walters, Prestwick, both of Scotland

[73] Assignee: British Technology Group Limited, London, England

[21] Appl. No.: 142,287

[22] PCT Filed: May 28, 1992

[86] PCT No.: PCT/GB92/00964

§ 371 Date: Nov. 19, 1993

§ 102(e) Date: Nov. 19, 1993

[87] PCT Pub. No.: WO92/21236

PCT Pub. Date: Dec. 10, 1992

[30] Foreign Application Priority Data

May 31, 1991 [GB] United Kingdom ............... 9111794

[51] Int. Cl.⁶ .................................................. A01N 33/04
[52] U.S. Cl. .......................................... 514/671; 514/631
[58] Field of Search .............................. 514/671, 631; 564/509, 225

[56] References Cited

U.S. PATENT DOCUMENTS

| | | | |
|---|---|---|---|
| 2,415,020 | 1/1947 | Morey | 167/22 |
| 4,005,193 | 1/1977 | Green et al. | 424/168 |
| 4,760,091 | 7/1988 | Carson et al. | 514/561 |
| 4,778,813 | 10/1988 | Fenyes et al. | 514/357 |
| 5,283,367 | 2/1994 | Babiarz et al. | 564/509 |

FOREIGN PATENT DOCUMENTS

| | | |
|---|---|---|
| 0190105 | 8/1986 | European Pat. Off. |
| 0353752 | 2/1990 | European Pat. Off. |
| 0376819 | 7/1990 | European Pat. Off. |
| 2228395 | 9/1990 | Japan. |
| 1164041 | 6/1969 | United Kingdom. |
| WO92/21235 | 12/1992 | WIPO. |

OTHER PUBLICATIONS

Smith et al., J. of General Microbiology, 1990, 136, 985–992.
Patent Abstracts of Japan, vol. 14 No. 539. 28 Nov. 1990.
Chemical Abstracts, vol. 84 No. 1, 5 Jan. 1976. Abstract # 1710c. Noel et al "Potent inhibition of . . . ".

*Primary Examiner*—Shailendra Kumar
*Attorney, Agent, or Firm*—Nixon & Vanderhye

[57] ABSTRACT

Compounds having the formula (I) below:

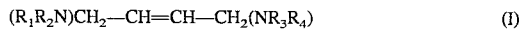

$$(R_1R_2N)CH_2-CH=CH-CH_2(NR_3R_4) \quad (I)$$

wherein $R_1$, $R_2$, $R_3$ and $R_4$, which may be the same or different represent hydrogen atoms, an alkyl group having from 1 to 6 carbon atoms, a cycloalkyl group of 3 to 6 carbon atoms, a heterocyclic group, an aryl group, a heteroaryl group having from 3 to 6 atoms, an amidino group or $R_1$, $R_2$ and/or $R_3$ and $R_4$ together represent a carbocyclic or heterocyclic group comprising from 3 to 6 atoms with the proviso that $R_1$, $R_2$, $R_3$ and $R_4$ cannot simultaneously represent hydrogen and salts thereof are fungicides especially mildewicides. Preferred compounds are those wherein the groups R represent methyl or ethyl groups.

7 Claims, No Drawings

ANTIFUNGAL COMPOUNDS

This application is a 371 of PCT/GB92/00964 filed May 28, 1992.

1. Field of the Invention

This invention is in the field of the control of fungal infection in plants.

2. Description of the Prior Art

Polyamines are essential for the growth and development of all organisms, including plants and fungi. However, whereas plants possess two pathways for polyamine biosynthesis, i.e. via the enzymes ornithine decarboxylase [ODC] and arginine decarboxylase [ADC], fungal polyamine biosynthesis appears to be a result of ODC activity only.

Plants are attacked by a wide range of fungi which are the cause of considerable losses of yield and quality. Since fungi possess only the ODC pathway of polyamine biosynthesis, the inhibition of this enzyme should control their growth.

Such inhibitors have been extensively researched but the major breakthrough was directly attributable to the synthesis of enzyme-activated irreversible inhibitors of ODC and ADC notably difluoromethylornithine [DFMO], which has been tested as an anti-cancer agent and also as an antiparasitic agent, and difluoromethylarginine [DFMA].

Recent work has shown that DFMO can reduce fungal growth and has led to the investigation of the use of DFMO as a fungicide, see for example N088/02986 (Weinstein and Galston) and U.S. Pat. No. 4,760,091 (Carson et al.).

The effect of compounds (including DFMO) which interfere with polyamine metabolism on the growth of the fungus *Botrytis cinerea* has been investigated (Smith et al., J. Gen. Microbiol. 1990, 136, 985). This work demonstrated that the DFMO inhibition of fungal growth could be reversed with the addition of putrescine, cadaverine, spermidine and spermine. "Butenediamine", caused some inhibition of fungal growth but significantly reversed the inhibitory effect of DFMO.

SUMMARY OF THE INVENTION

It has surprisingly been found that certain derivatives of 2-butene-1,4-diamine exhibit considerable anti-fungal activity. Accordingly, the invention provides the use as a fungicide of compounds having the general formula (I) below:

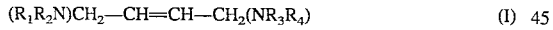

$$(R_1R_2N)CH_2—CH=CH—CH_2(NR_3R_4) \quad (I)$$

wherein $R_1$, $R_2$, $R_3$ and $R_4$, which may be the same or different represent a hydrogen atom, an alkyl group having from 1 to 6 carbon atoms, a cycloalkyl group having from 3 to 6 carbon atoms, a heterocyclic group, an aryl group, a heteroaryl group, having from 3 to 6 atoms or an amidino group or $R_1$ and $R_2$ and/or $R_3$ and $R_4$ together represent a carbocyclic or heterocyclic group comprising from 3 to 6 atoms, with the proviso that $R_1$, $R_2$, $R_3$ and $R_4$ cannot simultaneously represent hydrogen atoms.

DESCRIPTION OF THE PREFERRED EMBODIMENTS

The antifungal activity of the compounds of formula (I) is thought to be due mainly to their properties of polyamine metabolism interference. However, other mechanisms may play a role in the activity of these compounds as antifungal agents.

The groups $R_1$, $R_2$, $R_3$ and $R_4$ in formula (I) may be the same or different. Preferably the groups $R_1$ and $R_2$ identical and the groups $R_3$ and $R_4$ are identical and even more preferably, the groups $R_1$, $R_2$, $R_3$ and $R_4$ are all identical.

Preferred compounds are those wherein at least one of $R_1$, $R_2$, $R_3$ and $R_4$ are alkyl groups, preferably having 1 to 3 carbon atoms. More preferably at least one of $R_1$ and $R_2$ and at least one of $R_3$ and $R_4$ represents an alkyl group having from 1 to 3 carbon atoms.

A particularly preferred compound is E-(N',N'-dimethyl)-1,4diaminobut-2-ene.

Another preferred group of compounds are those wherein $R_1$, $R_2$, $R_3$ and $R_4$ all represent alkyl groups having from 1 to 4 carbon atoms. A particularly preferred compound is E-(N,N,N',N-tetraethyl)-1,4-diaminobut-2-ene (TED).

The compounds of formula (I) may be synthesised using the conventional techniques of synthetic organic chemistry. The substituted diamines may be synthesised by displacement of bromine from (E)-1,4-dibromo-2-butene by a primary or secondary amine.

The compounds of formula (I) also exhibit antifungal activity when prepared in the form of their acid salts and such salts may be utilised as fungicides according to this invention. The compounds can form salts with mineral acids such as HCl, HBr, HI, $H_2SO_4$, $HNO_3$, $H_3PO_4$ or with organic acids such as formic, acetic, trifluoroacetic, propionic, benzoic, maleic, fumaric, succinic, tartaric, citric, oxalic, glyoxylic, alkyl or aryl-sulphonic, salicylic, malonic and ascorbic. These salts may be prepared by standard techniques and procedures well known in the art.

The present invention also provides a method for the fungicidal treatment of plant material in either a preventative or curative mode. The treatment may be applied to growing or harvested plant materials. If the plant material is growing, then the plants may be treated before they are infected by the fungi. This can be carried out by either treating the whole plant (e.g. by spraying it with a solution/emulsion or suspension of the antifungal compounds) or by applying the compounds to specific parts of the plant, e.g. the leaves, stems, fruits or even seeds prior to planting. Treatment of the soil is another alternative since the antifungal compounds of the invention are systemic in their mode of action. Plants which have come into contact with fungi and thus already infected may be treated locally at site of infection or the whole plant may be treated.

The present invention also includes treatment of harvested plant parts for the control of fungal diseases. For this, various ways of carrying out the treatment can be employed. These will be well known to those skilled in the art, for example, treatment can be to the harvested plant itself by for example dipping the plant part into a solution of the antifungal agent, or by impregnating fungicide into the wrapper, carton, crate, etc. in which the plant will be transported. Alternatively, the harvested plant material may be fumigated with the fungicide in a special room, car or tank.

This invention also provides fungicidal compositions comprising at least one compound having the formula (I) together with a suitable diluent or carrier. Such diluents or carriers must not be phytotoxic to the plant materials. Suitable diluents and carriers include water and organic solvents. Preferably the concentration of the compounds is between 0.001–0.1 molar.

Seeds may be treated prior to planting and again this may be carried out among other methods by fumigation.

Thus, the compounds can be dispersed on a finely-divided solid to form a dust. Also, the compounds can be dispersed in water, typically with the aid of a wetting agent, and the resulting aqueous dispersion employed as a spray. In other procedures the compounds can be employed as a constituent of organic liquid compositions, oil-in-water and water-in-oil emulsions or dispersions, with or without the addition of wetting, dispersing or emulsifying agents.

Suitable adjuvants of the foregoing type are well known to those skilled in the art. The methods of applying the solid or liquid fungicidal formulations are similarly well known.

The concentration of the active compounds in solid or liquid compositions generally is from about 1 to about 20 percent by weight or more. Concentrations from about 5 to about 10 percent by weight are often employed. In compositions to be employed as concentrates, the active compound can be present in a concentration from about 15 to about 50 weight percent, preferably 20 weight percent. The compositions containing the active compounds can also contain other compatible additives, for example, phytotoxicants, plant growth regulants, pesticides, other fungicides and the like which are suitable for application to agricultural, horticultural, forestry and amenity crops. The present compositions can be applied by the use of power dusters, boom and hand sprayers, spray dusters and by other conventional means. The compositions can also be applied from airplanes as a dust spray since the ingredients are effective at very low application rates.

The exact rate to be applied is dependent not only on the specific diamine being applied, but also on the particular treatment desired (e.g. seed, soil, or foliage) the particular crop being treated, climatic conditions, severity of any infection and the like. Thus, it is also to be understood that all of the active compounds of the present invention and compositions containing the same may not be equally effective at similar concentrations or against the same fungal species.

In foliar treatments, the active compounds of the present invention are usually applied at an approximate rate of from about 50 to 500 g/ha, a rate of from about 80 to 400 g/ha being preferred and a rate of from about 100 to about 350 g/ha being particularly preferred.

In seed treatments, the active compounds of the present invention are usually applied at an approximate rate of from about 60 to about 250 g per 100 kg seed, a rate of from about 100 to about 200 g per 100 kg seed being preferred and a rate of from about 140 to about 180 g per 100 kg seed being particularly preferred.

In soil treatments, the active compounds of the present invention are usually applied at an approximate rate of from about 50 to about 350 g/ha, a rate of from about 100 to about 300 g/ha being preferred and a rate of from about 200 to about 280 g/ha being particularly preferred.

A typical solid composition is formulated by dry milling the active compound with BARDEN clay. This solid formulation or dust can contain the active compounds in amounts of from about 1 to about 25 percent by weight or more if desired. The dust is suitable for application to cereal seeds prior to planting.

A typical liquid composition is formulated by dissolving the active compound in a mixture of water and isopropanol (80:20 water/isopropanol ratio) containing a surfactant. This liquid formulation can contain the active compound in amounts of from about 15 to about 40 percent by weight or more if desired. The aqueous formulation is suitable for application to cereal foliage or application as a seed drench, after suitable dilution with water.

The invention will now be illustrated by the following Examples.

EXAMPLE 1

Synthesis of (E)-N,N,N',N'-Tetraethyl-1,4-daminobut-2-ene (TED) Dihydrobenzoate

The synthesis of the free base was carried out by the general procedure of J. J. Roberts and W. C. J. Ross (J. Chem. Soc., 1952, 4288). Diethylamine (3.285 g, 0.045 mol) was added during 15 min to a cooled solution (0° C.) of (E)-1,4-dibromobut-2-ene (1.07 g, 0.005 mol) (1) in benzene (5 ml). The product was diluted with chloroform (25 ml) and the organic layer was washed with water (4×25 ml). The chloroform layer was dried, filtered, and concentrated in vacuo to give (E)-N,N,N',N'-tetra-ethyl-1,4-diaminobut-2-ene as an oil (0.82 g, 82%). $\delta_H$ (90 MHz, CDCl$_3$) 1.10 (12H, t), 2.60 (8H, q), 3.20 (4H, m) and 5.75 (2H, m).

(E)-N,N,N',N'-Tetraethyl-1,4-diaminobut-2-ene (0.72 g, 3.6 mmol) was stirred with benzoic acid (0.87 g, 7.13 mmol) in benzene (5 ml) for 1 h. The precipitate was filtered and washed with ether to afford (E)-N,N,N',N'-tetraethyl-1,4-diaminobut-2-ene (TED) dihydrobenzoate as a white solid (1.11 g, 69%). $\delta_H$ (200 MHz, D$_2$O) 1.00 (12H, t), 2.90 (8H, q), 3.58 (4H, m), 5.89 (2H, m) and 7.34 (10H, m).

Other compounds were prepared by this method:

TED phosphate (0.56 g, 72%). $\delta_H$ (200 MHz, D$_2$O) 1.07 (12H, t), 3.00 (8H, q), 3.66 (4H, m) and 5.93 (2H, m).

TED fumarate (1.21 g, 68%). $\delta_H$ (200 MHz, D$_2$O) 1.09 (12H, t), 3.00 (8H, q), 3.66 (4H, m), 5.95 (2H, m) and 6.51 (2H, s).

TED propionate (0.72 g, 58%). $\delta_H$ (90 MHz, D$_2$O) 0.8 (6H, t), 1.0 (12H, t), 1.9 (4H, q), 2.9 (8H, q), 3.6 (4H, m) and 5.9 (2H, m).

(E)-N,N'-Diethyl-1,4-diaminobut-2-ene Dihydrobenzoate (free base 0.2 g, 28%) (salt 1.8 g, 33%). $\delta_H$ (90 MHz, D$_2$O) 1.2 (6H, t), 3.0 (4H, q), 3.6 (4H, m), 5.9 (2H, m) and 7.8 (10H, m).

(E)-N,N'-Dipropyl-1,4-diaminobut-2-ene Dihydrobenzoate (free base 0.73 g, 85%) (salt 1.25 g, 68%). $\delta_H$ (90 MHz, D$_2$O) 1.0 (6H, t), 1.6 (4H, m), 3.0 (4H, t), 3.6 (4H, m), 5.9 (2H, m) and 7.8 (10H, m).

(E)-N,N'-Dibutyl-1,4-diaminobut-2-ene Dihydrobenzoate (free base 0.45 g, 45%) (salt 2.03 g, 91%). $\delta_H$ (90 MHz, D$_2$O) 0.7 (6H, t), 1.3 (8H, m), 2.8 (4H, t), 3.5 (4H, m), 5.9 (2H, m) and 7.8 (10H, m).

EXAMPLE 2

Synthesis of (E)-N,N'-Dimethyl-1,4-diaminobut-2-ene Dihydrochloride

The synthesis of the free base was carried out by modifying the general procedure of J. J. Roberts and W. C. J. Ross (J. Chem. Soc., 1952, 4288).

(E)-1,4-Dibromobut-2-ene (2.14 g, 10 mmol) in benzene (50 ml) was added dropwise to a stirred solution of methylamine (30% w/v in methylated spirits, 21 ml, 200 mmol) in benzene (50 ml) at room temperature. The resulting solution was stirred for 24 h at room temperature, then chloroform (100 ml) was added and the solution was washed with water (3×100 ml). The organic layer was concentrated in vacuo to an oily residue which was partioned between chloroform (50 ml) and HCl (2M, 50 ml). The aqueous layer was decanted, washed with chloroform (2×25 ml) and concentrated to dryness in vacuo to afford (E)-N,N'-dimethyl-1,4-diaminobut-2-ene dihydrochloride (2.26 g, 82%). $\delta_H$ (90 MHz, D$_2$O) 3.09 (6H, s), 4.02 (4H, m) and 5.80 (2H, m).

EXAMPLE 3

(E)-N,N,N',N'-Tetraethyl-1,4-diaminobut-2-ene (TED) Dihydrobromide

Diethylamine (1.5 g, 20 mmol) in toluene (50 ml) was added to a stirred solution of (E)-1,4-dibromobut-2-ene (2.14 g, 10 mmol) in toluene (50 ml) at room temperature, and the solution was stirred for 4 h. The white precipitate formed was filtered off, washed with ether (2×20 ml), and dissolved in hot aqueous ethanol. The solution was allowed to cool and acetone was added. The white precipitate formed was filtered off and washed with acetone to yield (E)-N,N,N',N'-tetraethyl-1,4-diaminobut-2-ene (TED) dihydrobromide (2.16 g, 60%). $\delta_H$ (90 MHz, $D_2O$) 1.10 (12H, t), 3.15 (8H, q), 3.98 (4H, m) and 5.90 (2H, m).

EXAMPLE 4

(E)-N,N,-Diethyl-1,4-diaminobut-2-ene Dihydrochloride

This procedure was based on the work of D. J. Robins (J. Chem. Res. (S), 1983, 326).

Potassium phthalimide (18.5 g, 0.1 mol) was added in portions over 5 h to a stirred solution of (E)-1,4-dibromobut-2-ene (21.4 g, 0.1 mol) in acetone (200 ml) at 85° C. The suspension was stirred for 24 h at 85° C., then cooled and filtered. The filtrate was concentrated in vacuo to afford a white solid, which was recrystallised three times from acetone to yield (E)-1-phthalimido-4-bromobut-2-ene (15.76 g, 56.2%). $\delta_H$ (90 MHz, $CDCl_3$) 3.88 (2H, d), 4.28 (2H, d), 5.92 (2H, m) and 7.80 (4H, m).

The second stage of this synthesis was adapted from the procedure of K. Samejima, Y. Takeda, M. Kawase, M. Okada and Y. Kyogoku (Chem. Pharm. Bull., 1984, 32, 3428).

(E)-1-Phthalimido-4-bromobut-2-ene (4.2 g, 15 mmol), diethylamine (1.1 g, 15 mmol) and KF supported on Celite (7.5 g) were stirred together in acetonitrile (75 ml) at 40° C. for 18 h. The solution was filtered, and the filtrate was concentrated in vacuo to afford an oil, which was dissolved in glacial acetic acid (30 ml) and conc. HCl (30 ml). The mixture was heated at reflux for 30 h. The solution was cooled, filtered and the solvents were removed in vacuo to afford (E)-N,N-diethyl-1,4-diaminobut-2-ene dihydrochloride as an oil (1.32 g, 41%). $\delta_H$ (90 MHz, $D_2O$) 1.19 (6H, m) 3.24 (4H, q), 4.05 (4H, m) and 5.96 (2H, m).

EXAMPLE 5

Effect of E-(N,N,N',N'tetraethyl)-1,4-diaminobut-2-ene dihydrobromide (TED) and E-(N',N'-dimethyl)-1,4-diaminobut-2-ene dihydrobromide (DMD) on powdery mildew infection of barley seedlings Method Seeds of barley (Hordeum vulgare L Golden Promise) were sown in Fison's Levington compost in 36 cm seed trays. Plants were grown in a glasshouse under natural daylight supplemented for 16 h daily by 400 W mercury vapour lamps. The maximum temperature was 24° C. during the day and fell to a minimum of 9° C. at night. Plants at growth stage 12 (second leaf unfolded, Zadok's scale) were used for experiments. Seedlings were sprayed to run-off with solutions of the compounds containing 0.01% Tween 20. In all cases solutions were adjusted to pH 7.0 prior to spraying (using either sodium hydroxide of HCl). Sprays were applied using a Shandon spray unit either before or after inoculation with powdery mildew. Plants were inoculated with mildew conidia by shaking infected stock plants over them. Intensity of infection was assessed, 6, 8 and 10 days after inoculation by estimating the percentage leaf area infected using a standard area diagram. Barley powdery mildew normally sporulates 6–7 days after inoculation.

Both compounds gave substantial control of mildew infection of barley seedings. The results are shown in Table 1 below.

TABLE 1

| Treatment | % mildew infection days after inoculation | | |
|---|---|---|---|
| | 6 | 8 | 10 |
| Control | 4.1 ± 0.6 | 9.0 ± 0.8 | 13.9 ± 0.8 |
| TED, 1 mM | 0.9 ± 0.2 | 1.8 ± 0.1 | 3.9 ± 0.2 |
| DMD, 1 mM | 1.5 ± 0.1 | 1.9 ± 0.2 | 3.9 ± 0.3 |

EXAMPLE 6

The following compounds were tested for their effect on mildew infection in barley:

a) trans (N,N,N',N'-tetramethyl)-1,4-diaminobut-2-ene b) bis (amidino) trans 1,4-diaminobut-2-ene The post-inoculation treatment of seedlings was carried out as described in Example 5.

The results are shown in Table 2 below.

TABLE 2

| | % mildew infection |
|---|---|
| Control | 62.0 ± 4.4 |
| a | 29.3 ± 2.6 |
| b | 25.6 ± 1.7 |

The results show that the compounds have antifungal activity.

EXAMPLE 7

Effect of salts of TED on mildew infection of barley seedlings

Salts of TED prepared as described in Example 1 were tested for their effect on mildew infection of barley seedlings by the procedure described in Example 5. All compounds were applied as post inoculation sprays at 1 mM. Mildew infection was assessed at 8 days after inoculation. The results are shown in Table 3 below.

TABLE 3

| | % mildew infection on barley | % control |
|---|---|---|
| Control | 32.0 ± 2.5 | |
| E-TED benzoate | 16.1 ± 1.1 | 50 |
| E-TED phosphate | 12.6 ± 0.5 | 61 |
| E-TED fumarate | 12.8 ± 0.6 | 60 |
| E-TED propionate | 16.7 ± 1.2 | 48 |
| E-TED | | 80 |

EXAMPLE 8

The following compounds were tested for their effect on mildew infection in barley.

a) (E)-(N,N'-diethyl)-1,4-diaminobut-2-ene b) (E)-(N,N'-dipropyl)-1,4-diaminobut-2-ene c) (E)-(N,N'-dibutyl)-1,4-diaminobut-2-ene d) (E)-N'-ethyl-1,4-diaminobut-2-ene The post-inoculation treatment of seedlings was carried out as described in Example 5. The results are shown in Table 4 below.

TABLE 4

| Compound | % mildew infection of barley |
|---|---|
| Control | 16.0 ± 1.1 |
| a | 12.92 ± 0.7 |
| b | 13.73 ± 0.7 |
| c | 15.85 ± 1.3 |
| d | 12.96 ± 0.7 |

We claim:

1. A method of fungicidal treatment of plant material, which comprises applying to said material or to soil in which plants are growing or will be grown a fungicidal effective amount of a compound having the formula (I):

$$(R_1R_2N)CH_2-CH=CH-CH_2(NR_3R_4) \quad (I)$$

or a salt thereof wherein each of $R_1$, $R_2$, $R_3$ and $R_4$, which may be the same or different, represents an alkyl group having from 1 to 6 carbon atoms or $R_1$ and $R_3$ represent alkyl groups having from 1 to 3 carbon atoms or amidino groups and $R_2$ and $R_4$ represent hydrogen atoms.

2. The method of claim 1, wherein the groups $R_1$, $R_2$, $R_3$ and $R_4$ are identical.

3. The method of claim 1, wherein $R_1$, $R_2$, $R_3$ and $R_4$ represent alkyl groups having from 1 to 3 carbon atoms.

4. The method of claim 1, wherein the compound of formula (I) is E-(N, N,N',N'-tetraethyl)-1,4-diamino-2-butene.

5. The method of claim 1, wherein the compound of formula (I) is E-N,N'-dimethyl)-1,4-diaminobut-2-ene.

6. The method of claim 1, wherein said plant materials are seeds or harvested plant materials.

7. The method of claim 1, wherein said fungicidal treatment is to treat mildew and a mildewicidally effective amount of said compound is applied.

* * * * *